United States Patent [19]

Gibson et al.

[11] Patent Number: 5,041,601
[45] Date of Patent: Aug. 20, 1991

[54] PREPARATION OF ACYCLIC BIS (REISSERT COMPOUNDS)

[75] Inventors: Harry W. Gibson; Yajnanarayana H. R. Jois, both of Blacksburg, Va.

[73] Assignee: Virginia Tech Intellectual Properties, Inc., Blacksburg, Va.

[21] Appl. No.: 418,067

[22] Filed: Oct. 6, 1989

[51] Int. Cl.$^5$ ............... C07C 255/04; C07C 255/17; C07C 255/40
[52] U.S. Cl. .................... 558/392; 558/445
[58] Field of Search ................. 558/392, 445

[56] References Cited

U.S. PATENT DOCUMENTS

| | | | |
|---|---|---|---|
| 3,923,494 | 12/1975 | Teach | 558/445 X |
| 3,932,168 | 1/1976 | Stein et al. | 558/392 X |
| 3,966,789 | 6/1976 | Oishi et al. | 558/445 |
| 4,740,228 | 4/1988 | Kis-tamas et al. | 548/540 X |
| 4,785,019 | 11/1988 | Moore | 558/392 X |
| 4,929,713 | 5/1990 | Gibson et al. | 528/230 |

FOREIGN PATENT DOCUMENTS

| | | | |
|---|---|---|---|
| 0016453 | 1/1987 | Japan | 558/392 |
| 2177394 | 1/1987 | United Kingdom | 558/392 |

OTHER PUBLICATIONS

Gibson et al.; Amer. Chem. Soc., Polymer Preprints, 29(1), pp. 154–155, (1988).
Pandya et al.; Amer. Chem. Soc., Polymer Preprints, 30(1), pp. 206–207 (1989).
Gibson et al.; Amer. Chem. Soc., Polymer Preprints, 30(1), pp. 208–209 (1989).
McEwen et al.; J. Org. Chem. (1980), 45, pp. 1301–1308.
Gibson et al.; Amer. Chem. Soc., Polymer Preprints, 29(1), pp. 154–155 (1988).
Pandya et al.; Amer. Chem. Soc., Polymer Preprints, 30(1), pp. 206–207 (1989).
Gibson et al.; Amer. Chem. Soc., Polymer Preprints, 30(1), p. 208, (1989).
Voznesenskaya et al.; C.A., 87: 202161k (1977).
Rappoport-Editor, "The Chemistry of the Cyano Group", (1970), p. 76, Interscience Pub., N.Y.-London.
Weygand/Hilgetag, "Preparative Organic Chemistry", (1972), p. 519, John Wiley & Sons, N.Y.

Primary Examiner—Joseph Paul Brust
Attorney, Agent, or Firm—Richard P. Fennelly; Louis A. Morris

[57] ABSTRACT

A bis Reissert can be formed by the initial reaction of an aromatic dialdehyde (e.g., terephthaldicaboxaldehyde) and primary amine (e.g., methylamine) to form a reaction product which is then reacted with an acid chloride (e.g., benzoyl chloride).

2 Claims, No Drawings

PREPARATION OF ACYCLIC BIS (REISSERT COMPOUNDS)

BACKGROUND OF THE INVENTION

Recently, it has been proposed that Reissert compounds be synthesized to develop novel heterocyclic polymers for high performance applications (see H. W. Gibson et al., Amer. Chem. Soc., Polymer Preprints, 29(1), 154, 1988) Bis (Reissert compounds) have been synthesized in excellent yields by the use of a trimethylsilyl cyanide reagent and can be used to develop such polymers (see A. Pandya et al., Amer. Chem Soc., Polymer Preprints, 30(1), 206, 1989). Several novel 4,4'-coupled bis-isoquinolines have also been synthesized (see H W. Gibson et al., Amer Chem. Soc., Polymer Preprints, 30(1), 208, 1989).

W. E. McEwen et al., in J. Org. Chem 1980, 45, 1301-1308 discuss the synthetic uses of open-chain analogues of Reissert compounds by first preparing an aminonitrile by condensation of a primary amine with a cyanohydrin followed by reaction of the aminonitrile with an acid chloride to form the Reissert compound.

Chemical Abstracts, Vol. 87, 202161k reports on work by N. Voznesenskaya et al. in 1977 relating to the preparation of poly(phenyleneimidazolones) by polymerization of bis(alpha-aminonitriles) with aromatic dicarboxylic acid chlorides and subsequent cyclization of the prepared poly(alpha-cyanamides) by isomerization.

DESCRIPTION OF THE INVENTION

The instant invention relates to the formation of an open chain bis Reissert product of the reaction product of an aromatic dialdehyde, a primary amine, and a diacid chloride by: (a) the reaction of a dialdehyde, e.g., terephthaldicaboxaldehyde, with a primary amine, e.g., methylamine, in the presence of cyanide and bisulfite to yield a reaction product thereof; and (b) the reaction of the reaction product from (a) with an acid chloride to yield the bis Reissert product thereof.

The initial reaction of the instant process involves the reaction of a dialdehyde (e.g., terephthaldicaboxaldehyde) of the formula $$H(O)C-R-C(O)H$$

where R is aliphatic or aromatic with a primary amine R'NH$_2$, where R' alkyl, e.g., methyl, in the presence of a cyanide source (e.g., an alkali metal cyanide) and a bisulfite source (e.g., an alkali metal bisulfite). The reaction can be conducted at temperatures of from about −25° C. to about 100° C. using a molar ratio of dialdehyde to amine of from about 1:2 to about 1:2.5. The amount of cyanide and bisulfite, respectively, can range from about 1 to about 1.5 moles and from about 1 to about 1.5 moles per mole or reactants, respectively. The resulting reaction product, a bis(arylene aminoacetonitrile), has the formula

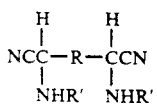

and is then used in the following step.

The reaction product described above is then reacted with an acid chloride of the formula $$R''C(O)Cl$$

where R'' is alkyl (e.g., a C$_4$-C$_6$ alkyl group) or aryl to yield the desired bis Reissert compound having the following formula:

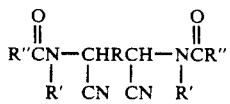

Where R is aliphatic or aromatic and R' and R'' are as defined above. This reaction step can be conducted at room temperature in a suitable organic solvent (e.g., dimethylformamide) and base to remove by-product hydrochloric acid.

The instant invention is further understood by the Examples which follow.

EXAMPLE 1

A mixture of water (600 ml) and sodium bisulfite (0.6 mole, 62.4 gm) in a two liter beaker equipped with a mechanical stirrer was stirred until solution was complete. Terephthaldicaboxaldehyde (0.3 mole, 40.24 gm) was added, and the mixture was stirred for one hour. Methylamine (0.6 mole, 20.2 gm, 50.5 ml of a 40% solution) was added and was further diluted by the addition of water (100 ml). This was followed by the addition of sodium cyanide (0.6 mole, 29.4 gm) over a thirty minute period. The reaction mixture was stirred overnight and the precipitate produced was filtered, washed with water and dried. Purified product was obtained by treatment once with activated carbon (NORIT brand) and crystallization from ethyl acetate. The crude yield of alpha, alpha'-dicyano-alpha, alpha'-bis (N-methylamino)-p-xylene was 40 gm (63%). It had a melting point of 130.5°–131.5°C.

IR (KBr): 3345-3200 (m, NH), 3000-2800 (m, aliphatic and aromatic C-H), 2224 (CN), 1484, 1462, 1447, 1425, 1412, 1300 cm$^{-1}$.

$^1$H NMR (CDCl$_3$): delta 7.59 (s, 4H, Ar-H), 4.8 (s, 2H CHCN), 2.58 (s, 6H, CH$_3$).

$^1$H NMR (DMSO-d$_6$): 7.53 (s, 4H, Ar-H), 5.07-4.99 (m, 2H, CHCN), 3.15-3.0 (m, 2H$_{1E}$NH), 2.34 and 2.32 (two singlets, 6H, CH$_3$).

Analysis: Theory: C 67.21%; H 6.59%; and N 26.15%. Found: C 67.21%; H 6.62%; and N 26.12%.

EXAMPLE 2

To a well stirring solution of the compound from Example 1 (0.01 mole, 2.143 gm) and pyridine (12 ml) in N-methyl-pyrrolidone (10 ml) under nitrogen atmosphere was added benzoyl chloride (0.02 mole, 2.32 ml) in five minutes at 0°-5° C. The reaction mixture was further stirred at room temperature for four days and was quenched by pouring into water (400 ml). Solids obtained were filtered, were washed with water, with 8% aqueous HCl, water, ethanol, and ether, respectively and were dried to obtain the product (4.22 gm, 100% yield). It was then crystallized from ethanol and had a melting point of 214°-215° C.

IR(KBr): 2910 (C-H), 1653, 1645 (N-CO), 1601, 1580 (aromatic), 1514, 1496, 1478, 1447, 1436, 1414, 1388, 1375, 1318, 1290, 1068, 1060 and 1028 cm$^{-1}$.

$^1$H NMR (DMSO-$d_6$): delta 7.64 (s, 4H, Ar-H), 7.6–7.45 (m, 10H, CO C$_6$H$_5$), 7.05–6.9 (s, 2H, CNCN), and 2.85 (s, 6H, CH$_3$).
Analysis: Theory: C 73.91%; H 5.25%; and N 13.27%. Found: C 73.94%; H 5.30%; and N 13.24%.
We claim:
1. A bis Reissert of the formula
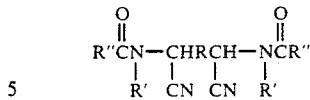
where R is arylene or alkylene and R' is alkyl and R" is alkyl or aryl.
2. A bis Reissert as claimed in claim 1 wherein R" is derived from benzoyl chloride.
* * * * *